(12) United States Patent
Becker et al.

(10) Patent No.: US 6,225,497 B1
(45) Date of Patent: May 1, 2001

(54) PROCESS FOR THE PHOSGENATION OF AMINES IN THE GAS PHASE USING MICROSTRUCTURE MIXERS

(75) Inventors: Gernot Becker, Dormagen; Konrad Fischer, Odenthal; Andreas Flink, Dormagen, all of (DE); Erhard Herrmann, Atizapan de Zaragoza (MX); Lothar Weismantel; Georg Wiessmeier, both of Köln (DE); Klaus Schubert, Karlsruhe (DE); Maximillian Fichtner, Oftersheim (DE)

(73) Assignees: Bayer Aktiengesellschaft, Leverkusen; Forschungszentrum Karlsruhe GmbH, Karlsruhe, both of (DE)

( * ) Notice: Subject to any disclaimer, the term of this patent is extended or adjusted under 35 U.S.C. 154(b) by 0 days.

(21) Appl. No.: 09/225,942

(22) Filed: Jan. 6, 1999

(51) Int. Cl.[7] .................................................. C07C 263/00
(52) U.S. Cl. ............................................... 560/347
(58) Field of Search ............................................. 560/347

(56) References Cited

U.S. PATENT DOCUMENTS

| | | |
|---|---|---|
| 4,289,732 | 9/1981 | Bauer et al. . |
| 4,847,408 | 7/1989 | Frosch et al. . |
| 5,117,048 | 5/1992 | Zaby et al. . |
| 5,391,683 * | 2/1995 | Joukar et al. . |
| 5,449,818 | 9/1995 | Biskup et al. . |
| 5,516,935 | 5/1996 | Bischof et al. . |
| 5,633,396 | 5/1997 | Bischof et al. . |
| 5,679,839 | 10/1997 | Armand et al. . |
| 5,803,600 | 9/1998 | Schubert et al. . |

FOREIGN PATENT DOCUMENTS 2236666   5/1997   (CA) .

OTHER PUBLICATIONS

Ind. Eng. Chem. Res., vol. 26, Jun. 1987, p. 1184.
Chem. Ing. Tech MS, 1708/88 (month unavailable).
Fortschr. Verf. Technek 23, (month unavailable) 1985, p. 373.
Chem. Eng. Sci. vol. 43, (month unavailable) 1988, p. 107.
J. Fluid Mech., (month unavailable) 1959, p. 113.

* cited by examiner

Primary Examiner—Paul J. Killos
(74) Attorney, Agent, or Firm—Joseph C. Gil; Lyndanne M. Whalen

(57) ABSTRACT

A process for rapidly mixing phosgene and an amine in the gas phase to produce the corresponding isocyanate. Microstructure mixers are used for the rapid mixing. The educts emerge from the micro-structure mixer in the form of thin free jets which mix very rapidly by diffusion and/or turbulence. As a result, the mixing operation is accelerated substantially as compared with conventional reactors. The isocyanate yield is also increased.

11 Claims, 3 Drawing Sheets

PROCESS FOR THE PHOSGENATION OF AMINES IN THE GAS PHASE USING MICROSTRUCTURE MIXERS

BACKGROUND OF THE INVENTION

The present invention relates to a process for the preparation of isocyanates by phosgenation of the corresponding amines in the gas phase using microstructure mixers for rapid mixing of the educts.

To carry out a chemical reaction in a continuous procedure, the reactants must be fed continuously to a chemical reactor and brought into intimate contact (i.e., mixed thoroughly) with the aid of a mixing element (mixer). As a rule, several reactions, so-called main and side reactions, proceed in the reactor when the reactants come into contact. The aim of the process engineer is to conduct the mixing and the reactions in a manner such that the highest possible yield of the desired product is achieved.

The quality of the mixing and the influence of the mixing element on the yield of the desired product depend on the ratio of the rate of the chemical reaction (determined by the reaction kinetics) to the rate of mixing. If the chemical reactions are slow reactions, as a rule the chemical reaction will be substantially slower than the mixing. The overall rate of reaction and the yield of desired product is then determined by the slowest step of the chemical reaction and by the mixing properties (residence time distribution, macromixing) of the chemical reactor used. If the rates of the chemical reactions and the rate of mixing are of the same order of magnitude, complex interactions between the kinetics of the reactions and the local mixing properties (determined by the turbulence in the reactor used and at the mixing element (micromixing)) arise. If the rates of the chemical reactions are substantially faster than the rate of mixing, the overall rates of the reactions and the yields obtained are substantially determined by the mixing (i.e., by the local time-dependent speed and concentration field of the reactants, the turbulence structure in the reactor and at the mixing element). (Brodkey, *Turbulence in Mixing Operations*, Academic Press, 1975).

According to the prior art, a number of mixing elements have been employed to carry out fast reactions in a continuous procedure. A distinction may be made here in principle between dynamic mixers (e.g., stirrers, turbines and rotor-stator systems), static mixers (e.g., Kenics mixers, Sch-aschlik mixers and SMV mixers), and jet mixers (e.g., nozzle mixers or T mixers). See, e.g., Chem. Ing. Tech. MS 1708/88; Fortschr. Verf. Technik 23,1985,373; and Ind. Eng. Chem. Res. 26,1987,1184.

For rapid mixing of starting substances in rapid reactions with the potential for undesirable secondary or side reactions, nozzle mixers are preferably employed. This particularly applies to reactions which proceed in the gas phase.

It has been known for a long time that isocyanates could be produced by reacting amines in the gas phase. However, gas phase reaction has acquired industrial importance only since the development of a process in which the problems of partial decomposition of polyfunctional amines during evaporation and of the tendency towards the formation of polymers during the phosgenation are eliminated (EP-A-289,840).

EP-A 0,289,840; 0,676,392; and 0,749,958 describe processes for the preparation of aliphatic di- and triisocyanates from the corresponding di- and triamines respectively by phosgenation in the gas phase. In these processes, the educt gas streams are passed into a tubular reactor for reaction. Mixing of the reactants takes place on entry into the tubular space through nozzles or a combination of a nozzle and an annular gap between the nozzle and tube. A Reynolds number of $Re \geq 4,700$ in the tube is taught to be an essential criterion for the mixing.

In EP-A 0,570,799, a jet mixer is used to mix the educts in the preparation of aromatic diisocyanates by phosgenation in the gas phase. EP-A 0,699,657 describes a multiple nozzle injection system for mixing the educts.

In the jet or nozzle mixers described in these disclosures, one of the two starting components is atomized into the other component(s) at a high flow rate. The kinetic energy of the sprayed stream is substantially dissipated behind the nozzle, i.e., it is converted into heat by turbulent breakdown of the stream into eddies and further turbulent breakdown of the eddies into ever smaller eddies. The eddies contain the particular starting components which are present side-by-side in the fluid balls (macromixing). A small degree of mixing by diffusion occurs at the edges of these initially larger structures at the start of the turbulent breakdown of the eddies. However, complete mixing is achieved only when the breakdown of the eddies has progressed to the extent that, when eddy sizes of the order of magnitude of the concentration microdimension (Batchelor length) (J. Fluid Mech. 5, 1959, 113; Chem. Eng. Sci. 43, 1988, 107) are reached, the diffusion is rapid enough for the starting components to be mixed completely with one another in the eddies. The mixing time required for complete mixing depends substantially on the specific energy dissipation rate, the characteristics of the specific materials and the geometry of the apparatus.

When nozzle or jet mixers are used in accordance with the prior art, the time for breakdown of the eddies elapses before complete mixing by diffusion. For very fast reactions, this means that either very high energy dissipation rates must be established in order to avoid undesirable side and secondary reactions, or, in the case of reactions with even higher rates of reaction, the corresponding reactions are not carried out to the optimum (i.e., only by-products or secondary products are formed).

SUMMARY OF THE INVENTION

It is an object of the present invention to provide a process for the preparation of isocyanates, preferably diisocyanates, triisocyanates and ether-(poly)isocyanates, by gas phase phosgenation of amines, preferably diamines, triamines and ether-(poly)amines.

It is also an object of the present invention to provide a process for the production of isocyanates in the gas phase in which mixing of the educts takes place rapidly and the formation of secondary products or by-products is suppressed or reduced.

It is another object of the present invention to provide a process for the production of isocyanates in which the educts are rapidly mixed homogeneously with one another so that, within the shortest time, local and time-related over-concentrations of the educts no longer occur.

It is a further object of the present invention to provide a gas phase phosgenation process for the complete reaction of the educts.

It is an additional object of the present invention to provide a gas phase phosgenation process for the production of isocyanates in which the formation of undesirable solid by-products that can lead to blockages and deposits is avoided.

These and other objects which will be apparent to those skilled in the art are accomplished by phosgenating the amine corresponding to the desired isocyanate in the gas phase in a microstructure mixer that rapidly mixes the amine educt with the phosgene educt.

DETAILED DESCRIPTION OF THE INVENTION

Figure 1:
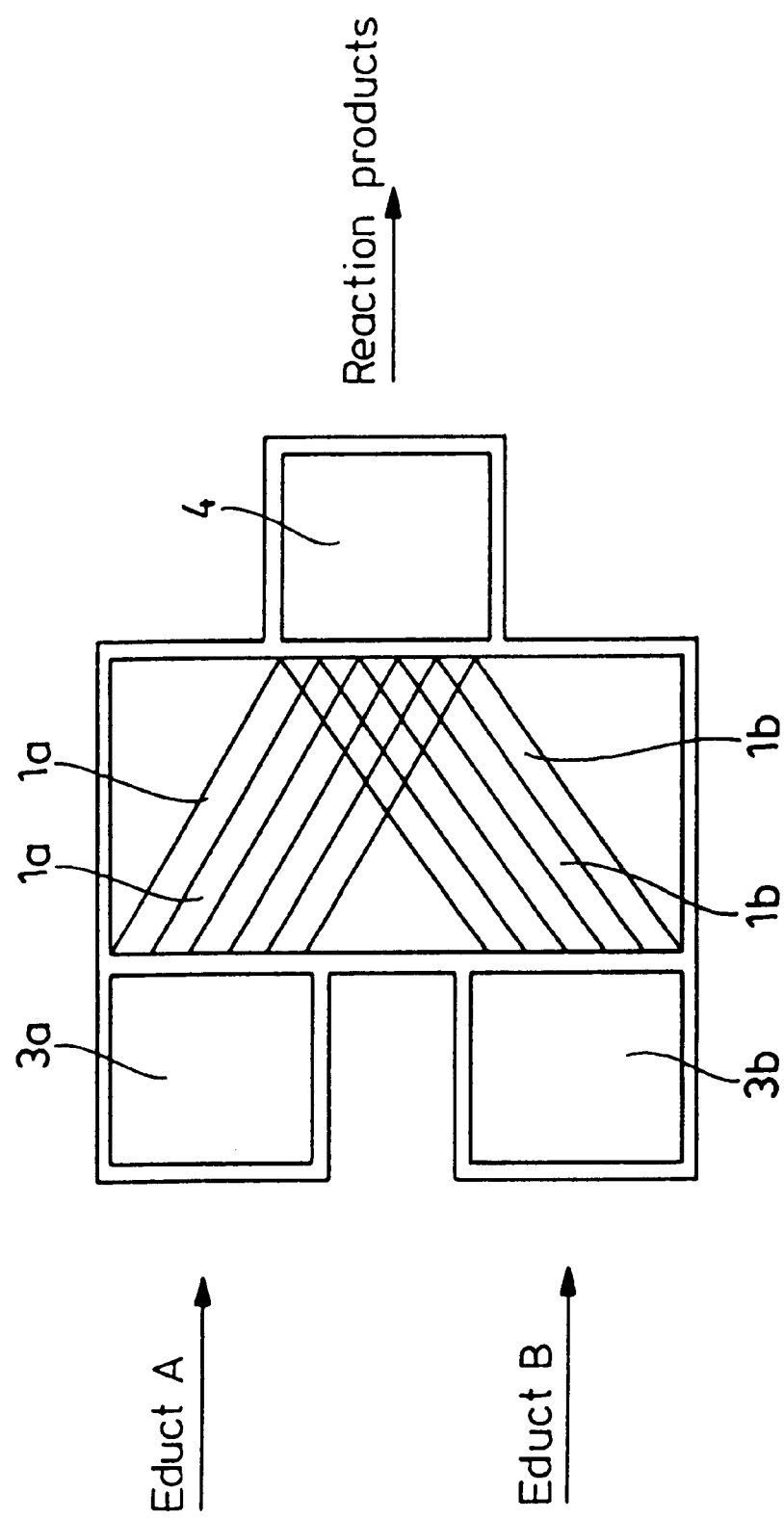
FIG. 1 illustrates the structure of a preferred embodiment of the microstructure mixer in which the phosgene and amine educts have symmetric flow paths.

The present invention relates to a process for the production of isocyanates by phosgenating the corresponding amines in the gas phase in a microstructure mixer.

An overall process for the preparation of (cyclo)aliphatic diisocyanates from (cyclo)aliphatic diamines and phosgene in which rapid mixing of the reactants is an important component step is described in U.S. Pat. No. 4,847,408 (corresponds to EP-A 0,289,840) which is incorporated herein by reference. A quite similar overall process for the preparation of aromatic diisocyanates from aromatic diamines is described in EP 0,570,799.

In the process of the present invention, the amine and phosgene educts and any inert gas employed are mixed by a mixing device, the characteristic mixing length of which is very small.

In a preferred embodiment of the invention, diisocyanates, triisocyanates and ether-(poly)isocyanates are produced by phosgenating the corresponding diamines, triamines and ether-(poly)amines in the gas phase using a microstructure mixer for rapid mixing of the diamine or triamine or ether-(poly)amine educt with the phosgene educt.

In the process of the present invention, diisocyanates of the formula

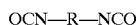
OCN—R—NCO    (I), are obtained by phosgenating the corresponding diamines of the formula

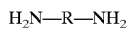
H₂N—R—NH₂    (II), in which
R represents a (cyclo-)aliphatic hydrocarbon radical having up to 15, preferably 3 to 13 carbon atoms, with the proviso that at least two carbon atoms are positioned between the two amino groups; or a hydrocarbon radical having at least one aromatic system.

A (cyclo-)aliphatic radical as used herein means aliphatic, cycloaliphatic, aliphatic-cycloaliphatic, cycloaliphatic-aliphatic radicals having carbon atoms which radicals are linked to the amino groups. Typical examples of suitable diamines are hexamethylene-1,6-diamine (HDA); 1-amino-3,3,5-trimethyl-5-aminomethyl-cyclohexane (IPDA); 4,4'-diaminodicyclohexylmethane; tetramethylene-1,4-diamine (BDA); pentane-1,3-diamine; 2,4-diamino-1-methylcyclohexane; and 2,6-diamino-1-methylcyclohexane (H6-TDA).

When R represents a hydrocarbon radical with at least one aromatic system, the aromatic system may be substituted by radicals such as alkyl groups, halogen atoms and/or ether groups. Typical examples of suitable diamines are toluene-2,4-diamine and toluene-2,6-diamine (TDA) and diphenylmethane-4,4'-diamine (MDA).

Triisocyanates represented by the formula

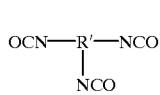
$$\text{OCN}—\underset{\underset{\text{NCO}}{|}}{\text{R}'}—\text{NCO} \qquad (III)$$

may be produced in accordance with the present invention by phosgenating the corresponding triamines represented by the formula

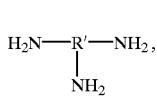
$$\text{H}_2\text{N}—\underset{\underset{\text{NH}_2}{|}}{\text{R}'}—\text{NH}_2, \qquad (IV)$$

in which
R' represents a saturated (cyclo)aliphatic hydrocarbon radical having up to 22, preferably from 7 to 11 carbon atoms, with the proviso that at least two carbon atoms are positioned between two amino groups.

The term (cyclo)aliphatic is intended to mean that both open-chain aliphatic and cycloaliphatic structural units can be present in the hydrocarbon radicals with it being possible for the amino groups to be bonded both aliphatically and cycloaliphatically. A typical example of a suitable triamine is 1,8-diamino-4-(aminomethyl)octane.

Ether-(poly)isocyanates represented by the formula

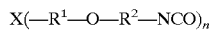
X(—R¹—O—R²—NCO)ₙ    (V), may be produced in accordance with the present invention by phosgenating the corresponding ether-(poly)amines represented by the formula

X(—R¹—O—R²—NH₂)ₙ    (VI), in which
x represents H, NH₂ or C(R³)₄₋ₙ;
R¹, R² and R³ each represents an optionally branched C₁–C₁₀-alkyl, C₃–C₂₄-cycloalkyl, C₇–C₂₄-aralkyl or C₆–C₂₄-aryl radical which is optionally substituted by Cl or Br and optionally contains one or more heteroatoms such as N, O, or S and
R¹ may also represent a direct bond from X to the ether-oxygen bonded to R²
and
n represents 1, 2 or 3.

A microstructure mixer of the type described in WO 95 304 76, DE-A 1,9541,266 or DE-A 19,540,292 and any other microstructure mixer which operates on the same principle as the mixers described in these disclosures may be used to carry out the process of the present invention.

When such a microstructure mixer is employed, the educt streams and any stream of inert gas are finely distributed and fine fluid threads are produced. These fluid threads emerge as free jets into the mixing or reaction space without the streams coming into contact with one another while they are within the microstructure mixer.

In carrying out the process of the present invention, mixing is carried out with a microstructure mixer in which the educts phosgene and amine educts are divided by a system of microchannels assigned to each of them into spatially separate fluid threads, and the fluid threads of the educts amine and phosgene educts emerge as free jets with flow rates which are the same for the particular educt into the mixing/reaction space. Each free jet of the phosgene educt is led into the mixing and reaction space immediately adjacent to a free jet of the amine educt. The adjacent free jets mix with one another by diffusion and/or turbulence.

The process can be carried out under an inert gas (e.g., $N_2$).

The microstructure mixer is preferably operated in a manner such that laminar flow conditions prevail.

An embodiment of the process of the present invention in which the gas threads of the educts emerge into the mixing/reaction space in alternate layers (alternately one above the other or side by side) and the thickness of the fluid threads of the educts on entry into the mixing/-reaction space is adjusted to a value between 10 $\mu$m and 1,000 $\mu$m, preferably 50 $\mu$m to 150 $\mu$m, has been found to be particularly suitable.

The microstructure mixer employed in carrying out the process of the present invention saves the time for turbulent eddy breakdown needed in prior art processes, and as a result, the mixing process is substantially accelerated.

The embodiment of the process of the present invention in which the educts leave the channels of the microstructure mixer isokinetically, (i.e., with the same flow rates) has been found to be particularly suitable. In this case, in particular, backflows are avoided and the formation of deposits and solids, which can lead to blocking of the component, cannot occur on the channel discharge openings of the microstructure mixer.

In an alternative for avoiding backflow and mixing of the educt components at the channel discharge openings of the microstructure mixer, a separating layer of inert gas is inserted between each of the fluid threads of the amine and phosgene educts. This alternative is described, for example, in WO 9,530,476.

In the phosgenation of polyfunctional amines, e.g., diamines, a compound which still contains an amine group in addition to the isocyanate group formed is formed as an intermediate product. This intermediate compound reacts with the diamine educt in a secondary reaction and competes with the phosgenation of the diamine to give a urea derivative.

If the diamine and phosgene educts are mixed only slowly, local over-concentrations of the educts are present during the comparatively long mixing time and monophosgenated diamine is surrounded in places by high concentrations of diamines, which leads to preferential formation of urea derivatives. To avoid this effect resulting from the slow mixing, high excesses of phosgene have been used in the prior art processes.

Accelerating the mixing operation reduces the mixing time during which local over-concentrations are present and therefore allows a reduction in the excess phosgene. Consequently, a correspondingly smaller amount of excess, highly toxic phosgene has to be separated off and recycled.

Further advantages of the process of the present invention include: (1) faster mixing and therefore a higher yield; (2) reduction in the proportion of by-products and therefore less formation of solids which can lead to blockages in the reaction space and the mixer; and as a result, (3) an increase in the service life of the equipment.

The present invention will be further described in detail with reference to the Figures.

FIG. 1 shows a diagram of a typical construction of a microstructure mixer such as that described in WO 9,530, 476. The construction principle of this mixer is based on various layers of the plates with microchannels running at an angle stacked vertically one above the other.

More specifically, a plate with micro-channels 1$a$ is followed in each case by a plate with micro-channels 1$b$, i.e., two plates arranged directly one above the other in the stack are in each case provided with a system of microchannels 1$a$ and 1$b$. The micro-channel systems of successive plates form an angle $\alpha$ with respect to one another and are arranged symmetrically to the horizontal axis in FIG. 1 (i.e., as mirror images to one another). The plates may, for example, have a thickness of about 100 $\mu$m. The cross-section dimensions of the microchannels are typically from about 70 to about 200 $\mu$m.

The micro-channels 1$a$ running upwards at an angle, seen from the center of the diagram in FIG. 1, open on the left into a distributor chamber 3$a$, to which an educt A can be fed. Analogously, micro-channels 1$b$ running downwards at an angle open on the left into a distributor chamber 3$b$, to which an educt B can be fed. The two systems of microchannels open on the right, without crossing each other, into a common mixing/reaction space 4. The mirror-symmetry arrangement of micro-channels 1$a$ and 1$b$ is not absolutely necessary. Micro-channels 1$b$ can, for example, have a different inclination towards the horizontal axis than micro-channels 1$a$.

However, it is important that the microchannels of a system be in each case the same as one another in terms of flow, that is, that all micro-channels 1$a$ have the same flow resistance. The same condition applies to the flow resistance of all micro-channels 1$b$. However, the flow resistances of the two microchannel systems 1$a$ and 1$b$ (in relation to one another) may be different. The same flow resistance is achieved, for example, if the length and the cross-section of all micro-channels 1$a$ are the same.

The educt, e.g., a gaseous reactant, fed to distributor chamber 3$a$ or 3$b$ is in each case distributed among the microchannels 1$a$ and 1$b$. The two reactants are brought together on entry into mixing/reaction space 4. This operation is described in more detail below with reference to FIG. 2.

Figure 2:
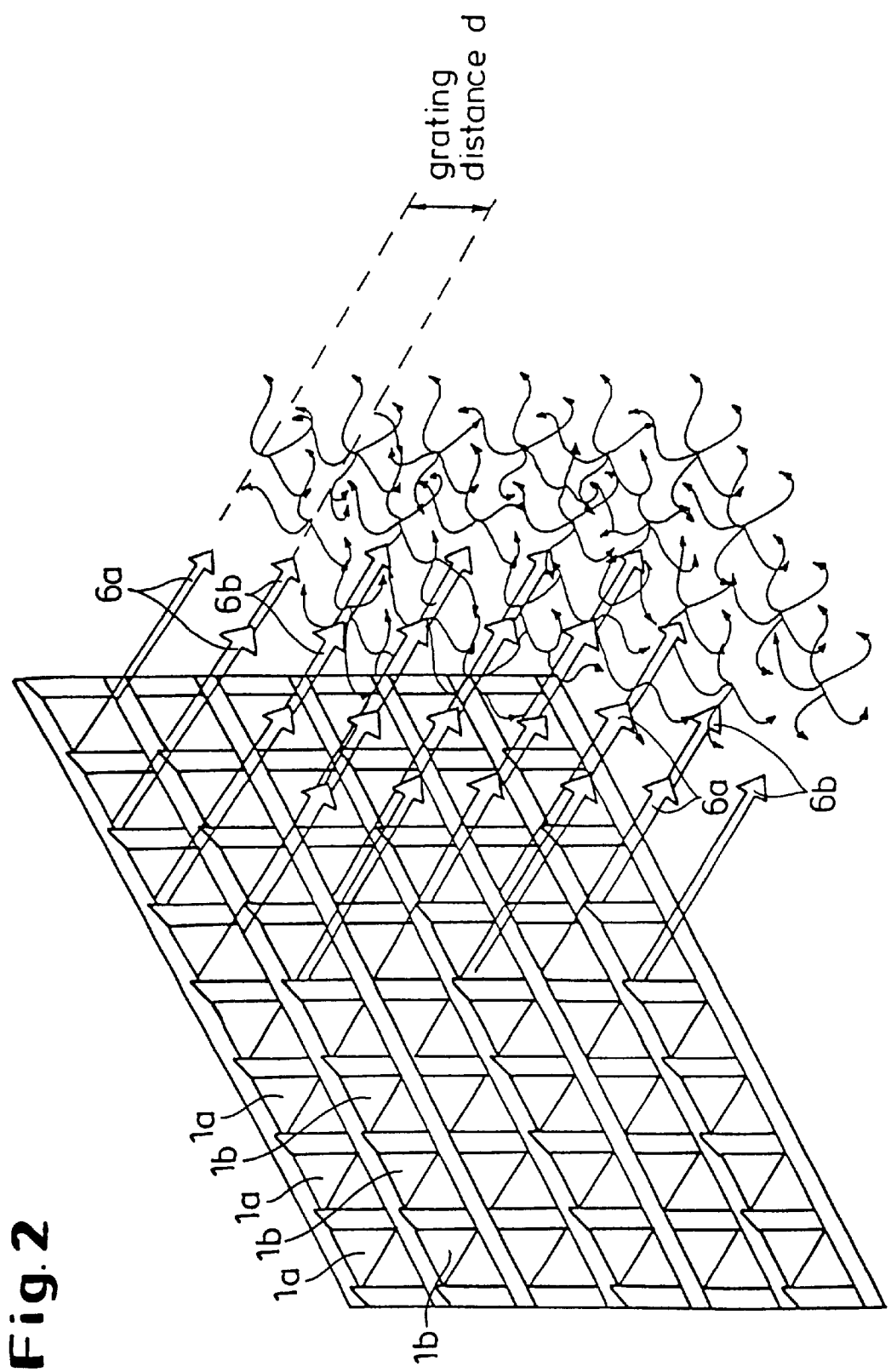
FIG. 2 illustrates the mixing of the free jets of amine and phosgene educts as they enter into the mixing or reaction space from the microstructure mixer.

FIG. 2 shows the opening cross-section of the microstructure mixer in perspective. In the top layer or plate, for example, micro-channels 1$a$ assigned to educt A, and in the subsequent layer or plate lying underneath, micro-channels 1$b$ of educt B each open into the mixing/reaction space. A layer or plate with the microchannels for educt A follows, and so on. FIG. 2 also shows how the fluid streams fed into the microchannels enter as free jets 6$a$ and 6$b$ into the mixing/reaction space and mix with one another at an increasing distance from the opening. Mixing is effected here by diffusion and/or turbulence. In the micro-channels, laminar flow conditions prevail as a rule. At the same time as the mixing, the reaction of educts A and B also starts. The reaction product is removed at the end of the mixing/reaction chamber (see FIG. 1.).

The micro-structure mixer illustrated in FIG. 1 can be modified so that in addition to the phosgene and amine educts, an inert gas is passed through the micro-mixer to the mixing/reaction space in the form of fluid threads. The fluid threads of the inert gas are passed through in a manner such that a free jet of the inert gas is always fed into the mixing/reaction space adjacent to a free jet of an educt.

Having thus described our invention, the following Example is given as being illustrative thereof.

EXAMPLE

The phosgenation of H$_6$-TDA (1-methyl-2,4-diaminocyclohexane) to H$_6$-TDI (1-methyl-2,4-diisocyanato-cyclohexane) was investigated as an example of a gas phase phosgenation.

The following main reaction proceeds in a homogeneous gas phase at 350° C.:

H$_6$-TDA+2 phosgene→H$_6$-TDI+4 hydrogen chloride

Figure 3:
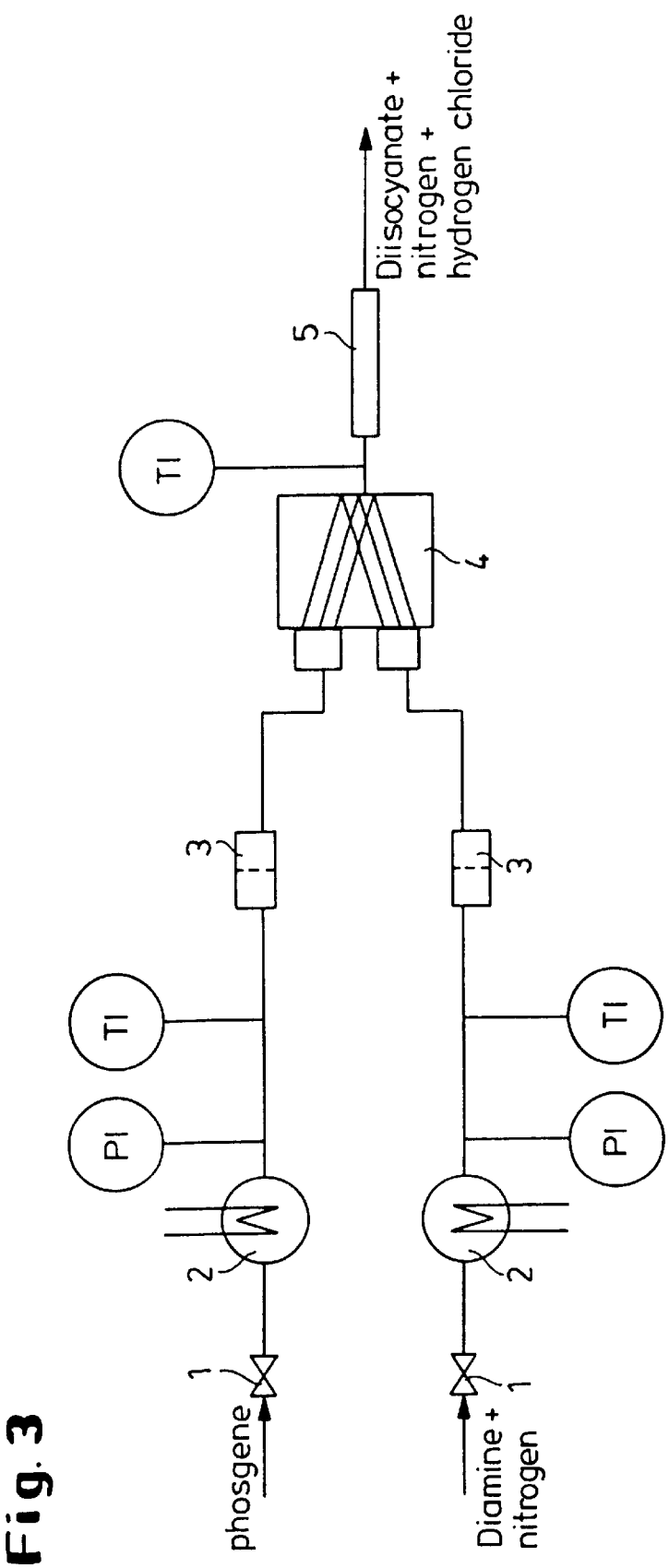
FIG. 3 is a flow diagram for an apparatus for investigating gas phase phosgenations using a microstructure mixer.

The investigation was carried out in the test apparatus shown in FIG. 3.

The apparatus shown in FIG. 3 in made up of two metering valves 1 (one for phosgene and one for amine), two super-heaters 2, in which the educts are brought to the reaction temperature, two fine filters 3, the micro-structure mixer 4 and a dwell tube 5. The reaction takes place in dwell tube 5. The microstructure mixer 4 employed has channels with a thickness of 70 μm, a channel width of 100 μm and a channel length of 14 mm. The mixer is made of 50 foils each with 50 channels per flow passage. The comparison was carried out with a conventional smooth jet nozzle in the laboratory.

To realize an isokinetic mode of operation of the microstructure mixer and at the same time, an excess of phosgene of 200%, the following molar streams were established:

* Phosgene: 6 mol/h

Diamine+nitrogen: 1 mol/h (diamine)+5 mol/h (nitrogen)=6 mol/h

In the experiments with the conventional smooth jet nozzle in the laboratory, a yield of 97% 1-methyl-2,4-diisocyanato-cyclohexane was achieved. In contrast, when the microstructure mixer required in the present invention was used, a yield of 99% was achieved. The yield reported in EP-A 676,392 is 96%.

These tests demonstrate that if a microstructure mixer is employed for the gas phase phosgenation, substantially fewer by-products are formed because of the faster mixing.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A gas phase process for the production of an isocyanate comprising reacting an amine with phosgene in the gas phase in a microstructure mixer for rapid mixing of the amine with phosgene.

2. The process of claim 1 in which a diisocyanate, a triisocyanate and/or an ether-(poly)isocyanate is produced.

3. The process of claim 1 in which a diamine, triamine and/or ether-(poly)amine is employed as the amine.

4. The process of claim 1 in which the microstructure mixer divides the phosgene and amine into alternating, spatially separated fluid threads that emerge as free jets having the same flow rate into a common mixing and reaction space in a manner such that the adjacent free jets mix with one another by diffusion and/or turbulence.

5. The process of claim 4 in which one or both of the reactant streams is diluted with an inert gas.

6. The process of claim 4 in which laminar flow conditions for the amine and phosgene are maintained in the microstructure mixer.

7. The process of claim 4 in which the fluid threads of the phosgene and amine emerge into the mixing/reaction space in layers lying alternately one above the other or side by side.

8. The process of claim 4 which the thickness of the fluid threads on entry into the mixing/reaction space is adjusted to a value of from about 10 μm to about 1,000 μm.

9. The process of claim 4 in which the thickness of the fluid threads on entry into the mixing/reaction space is adjusted to a value of from about 50 μm to about 150 μm.

10. The process of claim 1 in which a fluid thread of an inert gas is additionally fed adjacent to the fluid thread of an educt.

11. The process of claim 1 which the phosgene and amine emerge isokinetically from the microstructure mixer.

* * * * *